United States Patent
Kumar et al.

(10) Patent No.: US 11,013,224 B2
(45) Date of Patent: May 25, 2021

(54) SUBSTANCE AND COMPOSITION FOR VETERINARY PURPOSE

(71) Applicant: DubaiOmics FZ LLC, Dubai (AE)

(72) Inventors: Lekha Anil Kumar, Dubai (AE); Sharika Pariyachery, Sharjah (AE); Hans Meijer, Dubai (AE)

(73) Assignee: DUBAIOMICS FZ-LLC, Dubai (AE)

( * ) Notice: Subject to any disclaimer, the term of this patent is extended or adjusted under 35 U.S.C. 154(b) by 0 days.

(21) Appl. No.: 16/377,823

(22) PCT Filed: Oct. 10, 2017

(86) PCT No.: PCT/IB2017/001245
§ 371 (c)(1),
(2) Date: Apr. 8, 2019

(87) PCT Pub. No.: WO2018/069761
PCT Pub. Date: Apr. 19, 2018

(65) Prior Publication Data
US 2020/0093112 A1    Mar. 26, 2020

Related U.S. Application Data

(63) Continuation of application No. PCT/IB2017/001245, filed on Oct. 10, 2017.

(30) Foreign Application Priority Data

Oct. 10, 2016 (EP) .................................... 16193172

(51) Int. Cl.
| | | |
|---|---|---|
| *A01L 15/00* | (2006.01) | |
| *A61K 31/352* | (2006.01) | |
| *A61K 9/00* | (2006.01) | |
| *A61K 9/06* | (2006.01) | |
| *A61K 47/02* | (2006.01) | |
| *A61K 47/44* | (2017.01) | |
| *A61K 47/46* | (2006.01) | |

(52) U.S. Cl.
CPC ............ *A01L 15/00* (2013.01); *A61K 9/0017* (2013.01); *A61K 9/06* (2013.01); *A61K 31/352* (2013.01); *A61K 47/02* (2013.01); *A61K 47/44* (2013.01); *A61K 47/46* (2013.01)

(58) Field of Classification Search
CPC ...... A61K 31/352; A61K 47/02; A61K 47/44; A61K 47/46; A61K 9/0014; A61K 9/0017; A61K 9/06; A61P 17/00; A01L 15/00
See application file for complete search history.

(56) References Cited

U.S. PATENT DOCUMENTS

| | | | |
|---|---|---|---|
| 3,887,702 | A | 6/1975 | Baldwin |
| 4,070,451 | A | 1/1978 | Price |
| 4,996,043 | A | 2/1991 | Adamich-Saltman |
| 5,962,416 | A | 10/1999 | Buonomo |
| 2002/0182263 | A1 | 12/2002 | Stenti et al. |
| 2006/0173071 | A1 | 8/2006 | Owen |
| 2009/0304648 | A1 | 12/2009 | Owen |

FOREIGN PATENT DOCUMENTS

| | | | | |
|---|---|---|---|---|
| EP | 1787637 A2 | * | 5/2007 | ......... A61K 2300/00 |
| FR | 2665836 | | 2/1992 | |
| FR | 2984746 A1 | * | 6/2013 | ............ A61K 36/54 |
| WO | 99/00140 | | 1/1999 | |
| WO | 2010/080913 | | 7/2010 | |
| WO | 2010/126544 | | 11/2010 | |

OTHER PUBLICATIONS

English translation of FR-2984746-A1, publ. 2013, pp. 1-14 (Year: 2013).*
Anonymous: "Conditioning Hoof Cream", Equine Botanicals, Aug. 9, 2016 (Aug. 9, 2016), <https://web.archive.org/web/20160809232801/http://equinebotanicals.com/productspage/product-category/conditioning-hoof-cream/equinebotanicals.com>.
"Anonymous: "CothiVet Veterinary Information", Drugs.com, Jul. 4, 2010 (Jul. 4, 2010), <https://web.archive.org/web/20100704144343/https://www.drugs.com/vet/cothivet.html>".
"Anonymous: "CothiVet Wound cleaner & bitter spray" Jul. 10, 2017 (Jul. 10, 2017), <http://www.zoovet.ee/product/docs/2645777729.pdf".
"European Patent Office "Extended European Search Report" for EP Application No. EP16193172.0, dated Jul. 26, 2017", European Patent Office "Extended European Search Report" for EP Application No. EP16193172.0, dated Jul. 26, 2017.
"International Search Report and Written Opinion of the International Searching Authority from Int. App. No. PCT/IB/2017/001245, dated Feb. 20, 2018", International Search Report and Written Opinion of the International Searching Authority from Int. App. No. PCT/IB/2017/001245, dated Feb. 20, 2018.

* cited by examiner

*Primary Examiner* — Sarah Pihonak
(74) *Attorney, Agent, or Firm* — Dentons Durham Jones Pinegar; Sarah W. Matthews

(57) ABSTRACT

The present invention relates to cromoglycate and a salt thereof and compositions for the prophylactic and/or therapeutic treatment of a dry hoof condition and/or for use in increasing hoof growth in ungulates. Cromoglycate and a salt thereof and the compositions are useful to treat and maintain hooves in healthy condition.

17 Claims, 6 Drawing Sheets

SUBSTANCE AND COMPOSITION FOR VETERINARY PURPOSE

TECHNICAL FIELD

The present invention relates to cromoglycate and a salt thereof and compositions for use in increasing hoof growth in ungulates. Cromoglycate and a salt thereof and the compositions are useful to increase hoof growth and thereby achieve an improved hoof quality.

DETAILED DESCRIPTION

Figure 1:
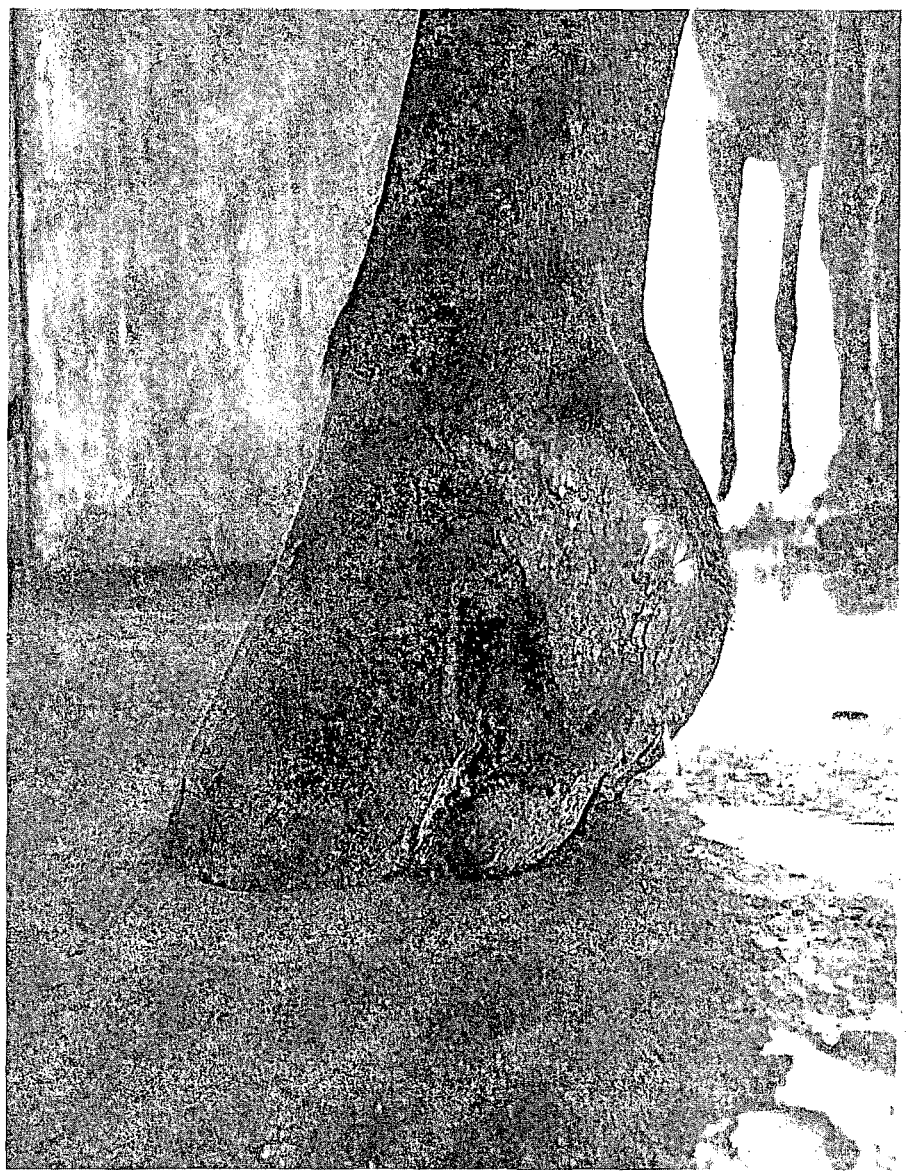
FIG. 1 is a picture of a hoof after the reset period.

The hoof is considered as a window into the animal's state of health. A hoof of good quality should have a smooth, shiny wall and have prominent and even growth rings, the tubules of the wall can be seen as parallel lines that run from coronary band to the base. The hoof wall should be free from flares, cracks, ripples, grooves and bulges.

The hoof is a complex structure comprising the hoof capsule, sole, frog, digital cushion and internal structures such as bone, cartilage, tendons and connective tissue.

The hoof wall is made from keratinized epithelial cells, which overlay the sensitive lamellar corium tissue containing water in addition to numerous electrolytes [4]. The outer wall of the hoof is made up of keratinized epithelial cells that run parallel to each other from the coronary band to the ground. These cells give the hoof its hard and horny surface.

The coronary band is the source of growth for the hoof wall. It is directly above the hoof wall and protected by a thick layer of skin and dense hair. Any major change in exercise, feed, moisture content, health status and general condition of the animal will affect the coronary band and change the growth rate of the hoof. Injury to the coronary band can result in irregular growth of the hoof wall and can develop into a permanently unsound hoof wall. The coronary band is an essential tissue in hoof development.

The sole, like the hoof wall, is a horn-like substance that protects the sensitive inner portions of the foot, but slightly softer. Sole is the first line of defense between the horse and the ground, its proper management is crucial to soundness. It should be form, slightly concave, of uniform texture and thicker in the toe and heel areas. The sole, as the foot is on the ground, should form a dome-like structure, providing support and strength to the hoof wall. The blood supply for the sole comes through the coronary band.

The frog is a soft, elastic v-shaped structure that should always have contact with the ground when the foot is bearing weight. The frog is located between the heels, forming a "V" into the centre of the sole. The frog is a spongy, flexible pad and is a weight-bearing surface, being the intermediate organ between the plantar cushion and the ground. The frog is differentiated from the sole of the foot by two lines called commissures. Commissures are deep crevices beside the frog, bordered by the bars on the outer edge. The condition of the frog is a good indicator of the health of the foot. A frog of good quality should be tough, have rubbery texture with around 50% moisture to give sufficient flexibility, expansion and ground contact to facilitate the good blood circulation shock absorption. Better ground contact of frog helps in proprioception. Proprioception is a neurological function that helps with movement. There are special receptors in the heel area above the frog that are part of that system. Inside the hoof wall and the sole is a delicate support structure made up of bones, cartilage and tendons that all depend upon the healthy exterior of the hoof for support and protection [5]. Lack of circulation or damaged frog can damage or kill the nerve cells and affect the neurosensory ability of the hoof and biomechanical feedback mechanisms. Support by the hoof to limb blood circulation comes out of the frog, the blood to be pumped up is provided through the coronary band. The coronary band drives hoof wall growth and plays a pivotal role in the blood supply of all hoof tissues.

Keratin is a key component and imparts strength and flexibility to the hoof. The keratin must be maintained in a flexible state and kept from drying out and becoming brittle as it does in a dry hoof condition, where the keratin of the hoof becomes brittle it loses its flexibility and has a tendency to crack or split. Horse hoof cracks can be caused by essentially anything that impairs the elasticity of the hoof weakens it or causes overloading.

A dry hoof condition increases the tendency of the hoof to crack or to break. In particular, fungi, cracks, dryness and too much moisture does not allow healthy hoof development and might cause accelerated decomposition of the hoof, this permits moisture absorption in wet climate and dryness in dry climate which can damage the hoof support structure and cause internal hoof problems. In dry climates or hooves suffering from a condition cracks, brittleness and dry hoof conditions occurs. Such a dry condition causes damage to the hooves and does not permit for a healthy hoof and does not permit the surface of the hoof to grow properly. The resulting damage is very painful to the animals, but also difficult, very expensive and time-consuming to repair. The hoof can be kept flexible by controlling its water content and maintaining the water balance. Consequently, it is desirable to maintain a healthy hoof condition of good quality with a healthy hoof growth and a balanced hoof moisture content to prevent fungi growth, microbial infection, cracking, brittleness and dryness for a healthy hoof.

The main tools in hoof management are hoof wall dressings and supplements. Hoof dressings are used to remedy cracks, splits and to avoid moisture loss. Hoof dressings are mostly applied to the hoof wall, and not to the coronary band. The coronary band drives both hoof wall growth as well as effects the development of all hoof tissues via blood supply. Most dressings have a barrier effect and give a shiny appearance [8] [19] [13]. There are three categories of hoof wall dressings used to preserve moisture loss: petroleum oil based dressing, pine tar or turpentine and lanolin based dressing, which have the consistency of hand lotion and the third category dressings contains specific drying agents like acetone. Some dressings have an antiseptic compound to prevent infection. Most hoof dressings extract the natural moisture, The moisture extraction protects the well visible hoof wall, but adversely affects the less apparent general hoof quality and functionality. A single means to address both hoof wall quality and general hoof quality and functionality would be desirable.

Another commonly used tool to improve hoof quality is the addition of supplements to the animal's feed. The hoof is a metabolically active tissue and common dietary deficiencies and imbalances influence hoof quality [8]. Dietary hoof supplements are thought to provide the nutritional building blocks to build healthy hooves and mostly include biotin, methionine, zinc, and evening primrose oil [15]. Hoof supplements can improve hoof quality, but the action of supplements on hoof quality is indirect and quality strongly relies on good digestion and circulation. A method to directly improve hoof health independently of digestion and circulation would be desirable.

The main functions of the hoof are to balance and to improve traction during movement, to support limb circulation and to act as a neurological and immunological sensory organ. In horses there has traditionally been a focus on hoof conformation, as hoof conformation can be easily measured, can be manipulated directly by a farrier and directly impacts movement efficiency and soundness (i.e. wrong conformation causes lameness). For a farrier to be able to manipulate the hoof, sufficient hoof growth is required. In horses in training often hoof growth slows down; the farrier cannot adjust the hoof, leading to underperformance and lameness of the horse.

Various approaches have been used to maintain a hoof of good quality, in particular to minimize hoof cracks. Typically, a treatment involves an attempt to remove pressure from the free extremity of the crack and immobilize its edges. A large number of formulations are available useful for the treatment of the dry hoof problem. Most of these formulations are based on the concept of sealing the surface of a hoof to prevent water loss and retain moisture already in the hoof.

U.S. Pat. No. 4,996,043 discloses a composition for correcting dry hoof for maintaining the hooves in a healthy condition which comprises an aqueous dispersion of triglycerides, polysaccharides, silicon oil and an antifreeze.

U.S. Pat. No. 4,070,451 discloses a composition which is applied as moisturizing oil for maintaining or improving the condition of hooves, in particular to prevent or counteract drying-out, cracking or chipping of hooves.

U.S. Pat. No. 5,962,416 discloses the acceleration of hoof growth by administration of a compound having somatotropin-like activity or a compound causing the secretion of somatotropin in the animal.

WO2010/126544 discloses the use of cromoglycate sodium as mast cell stabilizer for the prevention or treatment of laminitis.

Sodium cromoglycate is a drug developed in the 1960's as an inhaled powder for the treatment of asthma and later for the treatment of allergic rhinitis, allergic conjunctivitis, inflammatory bowel disease and food allergy [18] [17]. The drug is mainly used in inhalers, nasal spray, nasal drops, eye drops and as oral capsules. A 2% ophthalmic solution is used to treat allergic conjunctivitis [9]. Oral capsules are used to treat inflammatory bowel disease and food allergy [6]. The topical use of the medicine is new and a recent trial conducted with topical formulation containing 4% sodium cromoglycate demonstrated the efficacy of the drug for treatment of skin allergies [23] [7]. A highly concentrated injectable form has been described to treat acute and chronic laminitis in horses [11].

Sodium cromoglycate is a mast cell stabilizer, which inhibits release of histamine and other inflammatory mediators [10]. In addition to its effects on mast cells, sodium cromoglycate inhibits macrophages, eosinophils, monocytes and platelets involved in the inflammatory response [14]. The drug is known to inhibit the release of inflammatory mediators, including cytokines from mast cells and the chemotactic migration of eosinophils and neutrophils to the inflammation site [16] [21]. Sodium cromoglycate is known to inhibit the release of beta-glucuronidase from macrophages in bronchoalveolar cells [1] Studies on the molecular mechanism of action showed that sodium cromoglycate impedes the function of chloride channel important for regulating cell volume and prevents extracellular calcium influx into the cytoplasm of the mast cells [2] [3] [14] [20] [22].

ADME (absorption, distribution, metabolism and excretion) studies in animals have shown that 10% of the administered dose via inhalation is absorbed from the respiratory tract and the rate of absorption from the respiratory tract is slower than the elimination rate. Hence, the drug remains effectively in the lungs to produce its local therapeutic effect and is then cleared rapidly from the systemic circulation. Intravenous administration resulted in a general distribution throughout the tissues with higher concentration in liver and kidney, followed by rapid clearance of the drug from the plasma [16].

Lacking from the prior art, however, there is an effective approach for treating hooves by increasing the rate of hoof growth and by increasing the hoof moisture content. The currently available tools for hoof management do not improve hoof growth and hoof moisture content and, thus, do not maintain or improve hoof quality sufficiently.

Thus, there is a need for improving hoof growth thereby improving hoof quality.

Accordingly, there is still a need for an effective composition and method for the prophylactic and therapeutic treatment of a hoof condition, characterized by a poor hoof growth and preferably a dry hoof condition, for healing cracks, brittle, drying and dryness, moisture problems in and around hooves, in particular sole, frog, wall and heel of the hooves, which composition and method are preferably fast acting, long lasting and easy to apply. Accelerating the rate of hoof growth in parallel to balancing the moisture content of the hoof is desirable, in particular for an animal to recover from a cracked or otherwise injured hoof to reduce the time to recover, but also to provide a good quality of a hoof, in particular when it is exposed to heavy load.

The underlying technical problem of the present invention is to provide a substance and a composition overcoming the above disadvantages, in particular for use in increasing hoof growth in ungulates, preferably in conjunction with treating a dry hoof condition, in particular for use in increasing the hoof moisture content. Preferably, said increase in hoof growth results in improvement of hoof quality.

The technical problem of the present invention is in particular solved by the subject matter of the independent claims.

Thus, the present invention provides in one aspect cromoglycate or salts thereof for use in increasing hoof growth in ungulates. In another aspect, the present invention provides a cromoglycate-containing composition for use in increasing hoof growth in ungulates. In another aspect, the present invention provides a cream composition for use in increasing hoof growth in ungulates, which cream composition comprises Centella extract, borax, olive oil, shea butter, bees wax and sunflower oil. In a particularly preferred embodiment the present invention provides a cromoglycate-containing composition, which is a cream composition and which comprises Centella extract, borax, olive oil, shea butter, bees wax and sunflower oil.

In the context of the present invention a cromoglycate-containing composition is a composition, which contains cromoglycate and/or a salt thereof. In the context of the present invention compositions of the present invention are cromoglycate-containing compositions or cream compositions of the present invention or said expression refers to both of said compositions, namely cromoglycate-containing compositions and cream compositions.

The present invention provides, thus, cromoglycate or a salt thereof for use in increasing hoof growth in ungulates, provides a cromoglycate-containing composition for use in increasing hoof growth in ungulates, and a cream composition comprising Centella extract, borax, olive oil, shea butter, bees wax and sunflower oil for use in increasing hoof growth in ungulates, in wherein in all three of these aspects said increased hoof growth is achieved while providing good hoof quality, in particular improving the hoof quality, in particular in comparison to an untreated hoof, preferably untreated hoof of good quality.

The present invention provides a substance, namely cromoglycate or a salt thereof, and compositions of the present invention, namely a cromoglycate-containing composition and a cream composition, that prevent the drying-out of hooves. The present invention also provides a substance, namely cromoglycate or a salt thereof, and compositions of the present invention, namely a cromoglycate-containing composition and a cream composition, that increase the hoof growth, preferably thereby preventing harmful hoof conditions to maintain hooves in a good quality. The present invention also provides a substance, namely cromoglycate or a salt thereof, and compositions of the present invention, namely a cromoglycate-containing composition and a cream composition, for use in increasing hoof growth and for additional treating a dry hoof condition by increasing the hoof moisture content. The present invention provides a substance, namely cromoglycate or a salt thereof, and compositions of the present invention, namely a cromoglycate-containing composition and a cream composition, which not only act to retain the moisture present in the hoof, but also acts to hydrate the hoof. The present invention provides a substance, namely cromoglycate or a salt thereof, and compositions of the present invention, namely a cromoglycate-containing composition and a cream composition, that promote at the same time the growth of the hoof and additionally is active against bacteria and fungi. The present invention further provides a substance, namely cromoglycate or a salt thereof, and compositions of the present invention, namely a cromoglycate-containing composition and a cream composition, for use in increasing hoof growth and optionally for increasing the hoof moisture content of hooves in ungulates, wherein the hoof quality is maintained and/or improved, in particular in comparison to untreated hooves. The present invention provides a substance, namely cromoglycate or a salt thereof, and compositions of the present invention, namely a cromoglycate-containing composition and a cream composition, for increasing hoof growth and hoof quality directly through one treatment, in particular for maintaining the hoof in a healthy water-balanced condition.

Advantageously, cromoglycate or the salt thereof, the cromoglycate-containing composition and the cream composition of the present invention are very effective in providing a good hoof quality, in particular improving hoof quality by increasing the hoof growth and, optionally, increasing the hoof moisture content. Surprisingly, the horn of the hoof improves in quality.

Surprisingly, cromoglycate or the salt thereof, the cromoglycate-containing composition and the cream composition of the present invention significantly reduces the cracking of hooves and significantly reduces the length of time required for an animal to recover from a cracked or otherwise injured hoof. It not only acts to retain moisture already in the hoof, but also hydrates the hoof and, thus, improves the hoof moisture content. The hoof treating compositions of the present invention are easy to apply and provide a hoof in a good quality, promotes growth which results in healing of the hoof, and improves its flexibility. Surprisingly, the horn of the hooves improves in quality and the growth of the hoof is stimulated. The use of cromoglycate or the salt thereof, the cromoglycate-containing composition and the cream composition of the present invention in the treatment of a dry hoof condition, hoof growth or a hoof-crack, significantly reduces the time to recover from such a condition by reducing the time typically, in particular without treatment or with conventional treatment, for hoof regrowth.

Cromoglycate or the salt thereof, the cromoglycate-containing composition and the cream composition of the present invention was identified to enhance micro-circulation and upon direct application to the coronary band improves hoof wall growth and general hoof quality.

Cromoglycate or a Salt Thereof:

In one aspect, the present invention relates in particular to cromoglycate or a salt thereof for use in increasing hoof growth in ungulates, preferably whereby the hoof quality is improved, in particular in comparison to untreated hooves preferably in comparison to untreated hooves of good quality.

In a preferred embodiment of the present invention, cromoglycate or a salt thereof increases the hoof growth in ungulates by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated hooves of good quality, preferably said percentage increase is achieved over a period of 2, 3, 4, 6, 8, 10 or 12 weeks, preferably at least 30 days.

In a preferred embodiment of the present invention, cromoglycate or a salt thereof is for use in increasing hoof growth in ungulates and additionally for the prophylactic and/or therapeutic treatment of a dry hoof condition by increasing the hoof moisture content.

In a preferred embodiment of the present invention, cromoglycate or a salt thereof is for use in the prophylactic and/or therapeutic treatment of a dry hoof condition by increasing the hoof moisture content.

In a preferred embodiment of the present invention, cromoglycate or a salt thereof increases the hoof moisture content higher than in untreated hooves, preferably in comparison to untreated hooves of good quality. In a preferred embodiment, cromoglycate increases the hoof moisture content by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated hooves of good quality, preferably said percentage increase is achieved over a period of 2, 3, 4, 6, 8, 10 or 12 weeks, preferably at least 30 days.

In one embodiment of the present invention, cromoglycate or a salt thereof is for use in the treatment, in particular for repairing, of a hoof-crack by increasing the hoof growth. Cromoglycate or a salt thereof can be used for the treatment of a hoof-crack solely or may be used in combination with conventional hoof-crack repair techniques.

In a preferred embodiment of the present invention, the salt of cromoglycate is sodium cromoglycate that means disodium cromoglycate or cromolyn sodium. In a preferred embodiment, cromoglycate is the free acid of cromoglycate that means cromoglicic acid.

In the context of the present invention, cromoglycate or a salt thereof is administered to the subject topically, by infusion, by inhalation, or by limb perfusion. In a preferred embodiment, cromoglycate or a salt thereof is for oral or topical administration, preferably for topical administration. In a preferred embodiment of the present invention, cromoglycate or a salt thereof is applied in form of a solid or liquid composition.

In a preferred embodiment of the present invention, cromoglycate or a salt thereof is formulated to compositions comprising at least 0.1 wt.-% of cromoglycate or a salt thereof, preferably at least 0.2 wt.-%, preferably at least 0.5 wt-%, preferably at least 1 wt.-%, preferably at least 2 wt.-%, preferably at least 5 wt.-% or preferably at least 10 wt.-%, based on the total weight of the composition.

In a preferred embodiment of the present invention, cromoglycate or a salt thereof is co-formulated or co-administered with a second active ingredient, preferably antihistamines, anti-inflammatory agents, or antimicrobial agents, in particular antibiotics, antivirals or antifungals, and combinations thereof.

In a preferred embodiment of the present invention, cromoglycate or a salt thereof is formulated in form of a solid or liquid cromoglycate-containing composition, preferably the cromoglycate-containing composition is a pharmaceutical composition.

Cromoglycate-Containing Composition:

In one aspect, the present invention provides a composition containing cromoglycate or a salt thereof for use in increasing hoof growth in ungulates, preferably whereby the hoof quality is improved, in particular in comparison to untreated hooves, preferably untreated hooves of good quality.

In a preferred embodiment of the present invention, the cromoglycate-containing composition increases the hoof growth by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated hooves of good quality, preferably said percentage increase is achieved over a period of 2, 3, 4, 6, 8, 10 or 12 weeks, preferably at least 30 days.

In a preferred embodiment of the present invention, the cromoglycate-containing composition is a pharmaceutical acceptable formulation, wherein the active ingredient cromoglycate or a salt thereof is contained in an effective dose so to achieve the intended purpose.

In a preferred embodiment of the present invention, cromoglycate or a salt thereof is present in the cromoglycate-containing composition from 0.1 to 99 wt.-%, preferably from 1 to 99 wt.-%, preferably from 10 to 99 wt.-%, preferably from 0.1 to 90 wt.-%, preferably from 0.1 to 80 wt.-%, preferably from 0.1 to 70 wt.-%, preferably from 0.1 to 60 wt.-%, preferably from 0.1 to 50 wt.-%, preferably from 0.1 to 40 wt.-%, preferably from 0.1 to 30 wt.-%, preferably from 0.1 to 20 wt.-%, preferably from 0.1 to 10 wt.-%, preferably from 0.1 to 5 wt.-%, preferably from 0.5 to 90 wt.-%, preferably from 1 to 90 wt.-%, preferably from 1 to 80 wt.-%, preferably from 1 to 70 wt.-%, preferably from 1 to 60 wt.-%, preferably from 1 to 50 wt.-%, preferably from 1 to 40 wt.-%, preferably from 1 to 30 wt.-%, preferably from 1 to 20 wt.-%, preferably from 1 to 10 wt.-%, preferably from 2 to 90 wt.-%, preferably from 2 to 80 wt.-%, preferably from 2 to 70 wt.-%, preferably from 2 to 60 wt.-%, preferably from 2 to 50 wt.-%, preferably from 2 to 40 wt.-%, preferably from 2 to 30 wt.-%, preferably from 2 to 25 wt.-%, preferably from 2 to 20 wt.-%, preferably from 2 to 10 wt.-%, preferably from 10 to 90 wt.-%, preferably from 10 to 80 wt.-%, preferably from 10 to 70 wt.-%, preferably from 10 to 60 wt.-%, preferably from 10 to 50 wt.-%, preferably from 10 to 40 wt.-%, preferably from 10 to 30 wt.-%, preferably from 10 to 20 wt.-%, based on the total weight of the composition. In a preferred embodiment of the present invention, the cromoglycate-containing composition comprises at least 0.1 wt.-% of cromoglycate or a salt thereof, preferably at least 0.2 wt.-%, preferably at least 0.5 wt-%, preferably at least 1 wt.-%, preferably at least 2 wt.-%, preferably at least 5 wt.-% or preferably at least 10 wt.-%, based on the total weight of the composition.

In a preferred embodiment of the present invention, the salt of cromoglycate in the cromoglycate-containing composition is sodium cromoglycate that means disodium cromoglycate or cromolyn sodium. In a preferred embodiment, cromoglycate in the cromoglycate-containing composition is the free acid of cromoglycate that means cromoglicic acid.

In a preferred embodiment of the present invention, the cromoglycate-containing composition is for use in increasing hoof growth in ungulates and additionally for the prophylactic and/or therapeutic treatment of a dry hoof condition by increasing the hoof moisture content.

In a preferred embodiment of the present invention, the cromoglycate-containing composition composition is for use in the prophylactic and/or therapeutic treatment of a dry hoof condition by increasing the hoof moisture content.

In a preferred embodiment of the present invention, the cromoglycate-containing composition increases the hoof moisture content higher than in untreated hooves, preferably in comparison to untreated hooves of good quality. In a preferred embodiment, the composition increases the hoof moisture content by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated healthy hooves, preferably said percentage increase is achieved over a period of 2, 3, 4, 6, 8, 10 or 12 weeks, preferably at least 30 days.

In a preferred embodiment of the present invention, the cromoglycate-containing composition is for use in the treatment, in particular for repairing, of a hoof-crack by increasing the hoof growth. The cromoglycate-containing composition can be used for the treatment of a hoof-crack solely or may be used in combination with conventional hoof-crack repair techniques.

In the context of the present invention, the cromoglycate-containing composition is administered to the subject topically, by infusion, by inhalation, or by limb perfusion. In a preferred embodiment of the present invention, the cromoglycate-containing composition is for oral or topical administration, preferably for topical administration, preferably for use in application to the external surface of a hoof and the frog adjacent thereto. In a preferred embodiment of the present invention, the cromoglycate-containing composition is applied in the form of a solid or liquid composition. In a preferred embodiment, the composition is formulated as an aqueous emulsion, a cream, a gel, a solution, a spray or a wax, preferably as a cream.

In a preferred embodiment of the present invention, cromoglycate or a salt thereof in the cromoglycate-containing composition is co-formulated or co-administered with a second active ingredient, preferably antihistamines, anti-inflammatory agents, or antimicrobial agents, in particular antibiotics, antivirals or antifungals, and combinations thereof.

In a preferred embodiment, the salt of cromoglycate in the composition is sodium cromoglycate.

In a preferred embodiment, cromoglycate in the composition is the free acid of cromoglycate that means cromoglicic acid.

Cream Composition:

In one aspect, the present invention provides a cream composition for use in increasing hoof growth in ungulates, wherein the cream composition comprises centella extract, borax, olive oil, shea butter, bees wax and sunflower oil, preferably whereby the hoof quality is improved, in particular in comparison to untreated hooves. In a preferred embodiment of the present invention, the cream composition is for use in accelerating hoof growth in ungulates.

In a preferred embodiment of the present invention, the cream composition increases the hoof growth by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated hooves of good quality, preferably said percentage increase is achieved over a period of 2, 3, 4, 6, 8, 10 or 12 weeks, preferably 30 days.

In a preferred embodiment of the present invention, the cream composition, wherein the cream composition comprises centella extract, borax, olive oil, shea butter, bees wax and sunflower oil, is for use in increasing hoof growth in ungulates and additionally for the prophylactic and/or therapeutic treatment of a dry hoof condition by increasing the hoof moisture content.

In a preferred embodiment of the present invention, the cream composition, wherein the cream composition comprises centella extract, borax, olive oil, shea butter, bees wax and sunflower oil, is for use in the prophylactic and/or therapeutic treatment of a dry hoof condition, preferably by increasing the hoof moisture content.

In a preferred embodiment of the present invention, the cream composition increases the hoof moisture content higher than in untreated hooves, preferably in comparison to untreated hooves of good quality. In a preferred embodiment, the hoof moisture content is increased by at least 1%, preferably at least 2%, preferably at least 3%, preferably at least 5%, preferably at least 10%, preferably at least 15%, preferably at least 20%, preferably at least 30%, in comparison to untreated hooves, preferably in comparison to untreated hooves of good quality, preferably said percentage increase is achieved over a period of 2, 3, 4, 6, 8, 10 or 12 weeks, preferably 30 days.

In a preferred embodiment of the present invention, the cream composition, wherein the cream composition comprises centella extract, borax, olive oil, shea butter, bees wax and sunflower oil, is for use in the treatment, in particular for repairing, of a hoof-crack, by increasing the hoof growth. The cream composition can be used for the treatment of a hoof-crack solely or may be used in combination with conventional hoof-crack repair techniques.

In a preferred embodiment of the present invention, the cream composition of the present invention comprises cromoglycate or a salt thereof.

In a preferred embodiment of the present invention, cromoglycate or a salt thereof is present in the cream composition from 0.1 to 99 wt.-%, preferably from 1 to 99 wt.-%, preferably from 10 to 99 wt.-%, preferably from 0.1 to 90 wt.-%, preferably from 0.1 to 80 wt.-%, preferably from 0.1 to 70 wt.-%, preferably from 0.1 to 60 wt.-%, preferably from 0.1 to 50 wt.-%, preferably from 0.1 to 40 wt.-%, preferably from 0.1 to 30 wt.-%, preferably from 0.1 to 20 wt.-%, preferably from 0.1 to 10 wt.-%, preferably from 0.1 to 5 wt.-%, preferably from 0.5 to 90 wt.-%, preferably from 1 to 90 wt.-%, preferably from 1 to 80 wt.-%, preferably from 1 to 70 wt.-%, preferably from 1 to 60 wt.-%, preferably from 1 to 50 wt.-%, preferably from 1 to 40 wt.-%, preferably from 1 to 30 wt.-%, preferably from 1 to 20 wt.-%, preferably from 1 to 10 wt.-%, preferably from 2 to 90 wt.-%, preferably from 2 to 80 wt.-%, preferably from 2 to 70 wt.-%, preferably from 2 to 60 wt.-%, preferably from 2 to 50 wt.-%, preferably from 2 to 40 wt.-%, preferably from 2 to 30 wt.-%, preferably from 2 to 25 wt.-%, preferably from 2 to 20 wt.-%, preferably from 2 to 10 wt.-%, preferably from 10 to 90 wt.-%, preferably from 10 to 80 wt.-%, preferably from 10 to 70 wt.-%, preferably from 10 to 60 wt.-%, preferably from 10 to 50 wt.-%, preferably from 10 to 40 wt.-%, preferably from 10 to 30 wt.-%, preferably from 10 to 20 wt.-%, based on the total weight of the composition. In a preferred embodiment of the present invention, the cream composition comprises at least 0.1 wt.-% of cromoglycate or a salt thereof, preferably at least 0.2 wt.-%, preferably at least 0.5 wt-%, preferably at least 1 wt.-%, preferably at least 2 wt.-%, preferably at least 5 wt.-% or preferably at least 10 wt.-%, based on the total weight of the composition. Surprisingly, the effect of a composition of the present invention on the hoof moisture content and the hoof growth can be significantly increased when cromoglycate is added.

In a preferred embodiment of the present invention, the salt of cromoglycate in the cream composition is sodium cromoglycate that means disodium cromoglycate or cromolyn sodium. In a preferred embodiment, cromoglycate in the cream composition is the free acid of cromoglycate that means cromoglicic acid.

In a preferred embodiment of the present invention, the cream composition contains at least 0.01 wt.-% of centella extract, preferably at least 0.05%, preferably at least 0.1%, preferably at least 0.2%, or preferably at least 0.5%, preferably from 0.01 to 10%, preferably from 0.01 to 5%, preferably from 0.01 to 1%, preferably from 0.01 to 0.1%, preferably from 0.05 to 10%, preferably from 0.05 to 5%, preferably from 0.05 to 1%, preferably from 0.05 to 0.1%, preferably from 0.1 to 1%, preferably from 0.1 to 0.5%, preferably from 0.1 to 5%, based on the total weight of the composition.

In the context of the present invention centella extract, preferably centella asiatica extract, is a propylene glycol extract of the leaves of Centella Asiatica. The active constituents are pentacyclic triterpenoids which helps in wound healing and stimulate collagen synthesis.

In a preferred embodiment of the present invention, the cream composition comprises 1 to 20 wt.-% of borax, preferably 1 to 15 preferably 1 to 10 wt.-%, preferably 1 to 8 wt.-%, preferably 1 to 6 wt.-%, preferably 1 to 4 wt.-%, preferably 2 to 20 wt.-%, preferably to 10 wt.-%, preferably 2 to 8 wt.-%, preferably 5 to 20 wt.-%, preferably 5 to 10 wt.-%, preferably 10 to 20 wt.-%, based on the total weight of the composition.

In a preferred embodiment of the present invention, the cream composition comprises at 1% of olive oil, preferably at least 2%, preferably at least 5%, preferably at least 10%, preferably at least 20%, preferably from 1 to 50%, preferably from 1 to 40%, preferably from 1 to 30%, preferably from 1 to 20%, preferably from 1 to 10%, preferably from 5 to 50%, preferably from 5 to 40%, preferably from 5 to 30%, preferably from 5 to 25%, preferably from 5 to 20%, preferably from 5 to 10%, preferably from 10 to 50%, preferably from 10 to 40%, preferably from 10 to 30%, preferably from 10 to 20%, preferably from 10 to 15%, based on the total weight of the composition.

In the context of the present invention olive oil is a vegetable oil obtained from the olive (Olea Europaea). Olive oil is rich in mono-unsaturated fatty acid (omega 9). In a preferred embodiment it is used as carrier oil and to adjust the consistency of cream. Olive oil preferably helps to keep in skin smooth and moisturised.

In a preferred embodiment of the present invention, the cream composition comprises at least 1% of shea butter, preferably at least 5%, preferably at least 10%, preferably at least 20%, preferably at least 30%, preferably from 1 to 50%, preferably from 1 to 40%, preferably from 1 to 30%, preferably from 1 to 20%, preferably from 1 to 10%, preferably from 5 to 50%, preferably from 5 to 40%, preferably from 5 to 30%, preferably from 5 to 25%, preferably from 5 to 20%, preferably from 10 to 50%, preferably from 10 to 40%, preferably from 10 to 30%, preferably from 10 to 25%, preferably from 10 to 20%, preferably from 20 to 50%, based on the total weight of the composition.

In the context of the present invention shea butter is a plant fat extracted from kernel of shea tree (Vitellaria Paradox) and has buttery consistency with moisturizing and emollient properties and spreads easily on the skin. Shea butter consists preferably of at least 90% triglycerides and 4 to 8% unsaponifiables. Triglycerides are responsible for the emollient properties while unsaponifiable fraction contains the bioactive substances that include tocopherol, sterol and alcohols responsible for the medicinal properties. Unrefined shea butter is preferably prepared using traditional extraction by boiling water and skimming of the released oil and does not include a refining step.

In a preferred embodiment of the present invention, the cream composition comprises wax, preferably bees wax. In a preferred embodiment, the composition comprises at least 1% of bees wax, preferably at least 5%, preferably at least 10%, preferably at least 20%, preferably at least 30%, preferably from 1 to 50%, preferably from 1 to 40%, preferably from 1 to 30%, preferably from 1 to 20%, preferably from 1 to 10%, preferably from 5 to 50%, preferably from 5 to 40%, preferably from 5 to 30%, preferably from 5 to 25%, preferably from 5 to 20%, preferably from 10 to 50%, preferably from 10 to 40%, preferably from 10 to 30%, preferably from 10 to 25%, preferably from 10 to 20%, preferably from 20 to 50%, based on the total weight of the composition.

In the context of the present invention bees wax is the natural wax produced by honey bees and is a product made form honey comb of bees. It is a moisturizer and can acts as a natural emulsifier along with borax in creams. Bees wax is known to have anti-inflammatory action. It is also used as viscosity enhancer in creams. The melting point of bees wax is preferably in the range of 62-64° C. Natural bees wax is preferably prepared by melting the honey comb, filtering it, separating out the water after cooling and solidification of the wax. Color of natural bees wax is yellow which originates from propolis and pollen colorants.

In a preferred embodiment of the present invention, the cream composition comprises at least 1% of sunflower oil, preferably at least 2%, preferably at least 5%, preferably at least 10%, preferably at least 20%, preferably from 1 to 50%, preferably from 1 to 40%, preferably from 1 to 30%, preferably from 1 to 20%, preferably from 1 to 10%, preferably from 5 to 50%, preferably from 5 to 40%, preferably from 5 to 30%, preferably from 5 to 25%, preferably from 5 to 20%, preferably from 5 to 10%, preferably from 10 to 50%, preferably from 10 to 40%, preferably from 10 to 30%, preferably from 10 to 20%, preferably from 10 to 15%, based on the total weight of the composition.

In the context of the present invention sunflower oil is a vegetable oil obtained from the sunflower (Helianthus annuus). Sunflower oil is a poly unsaturated oil (omega-6) rich in linoleic acid that is abundant in skin and preferably equilibrates with the endogenous pool of lipids and preferably has better moisturizing action.

In a preferred embodiment of the present invention, the cream composition contains at least 0.01 wt.-% of tea tree oil, preferably at least 0.05%, preferably at least 0.1%, preferably at least 0.2%, preferably at least 0.5%, preferably at least 1%, preferably from 0.01 to 5%, preferably from 0.01 to 1%, preferably from 0.01 to 0.5%, preferably from 0.01 to 0.1%, preferably from 0.02 to 5%, preferably from 0.02 to 2%, preferably from 0.02 to 1%, preferably from 0.02 to 0.5%, preferably from 0.02 to 0.1%, based on the total weight of the composition. In a further preferred embodiment of the present invention, the cream composition is free from tea tree oil.

In the context of the present invention tea tree oil is a volatile essential oil from the Australian native plant Melaleuca alternifolia. Tea tree oil preferably shows antimicrobial properties and is preferably used in creams for its antimicrobial action. Tea tree oil is used as a natural preservative in creams and lotions.

In a preferred embodiment of the present invention, the cream composition of the present invention comprises centella extract in the range of 0.05 to 5 wt.-%, borax in the range of 1 to 10 wt.-%, olive oil in the range of 5 to 20 wt.-%, shea butter in the range of 5 to 30 wt.-%, bees wax in the range of 5 to 30 wt.-%, tea tree oil of 0.02 to 2 wt.-% and sunflower oil in the range of 5 to 20 wt.-%, each based on the total weight of the composition.

In a preferred embodiment of the present invention, the cream composition of the present invention comprises centella extract in the range of 0.05 to 5 wt.-%, borax in the range of 1 to 10 wt.-%, olive oil in the range of 5 to 20 wt.-%, shea butter in the range of 5 to 30 wt.-%, bees wax in the range of 5 to 30 wt.-%, tea tree oil of 0.02 to 2 wt.-% and sunflower oil in the range of 5 to 20 wt.-% and cromoglycate sodium in the range of 1 to 25 wt.-%, each based on the total weight of the composition.

In a preferred embodiment of the present invention, the cream composition of the present invention comprises centella extract in the range of 0.1 to 0.5 wt.-%, borax in the range of 2 to 8 wt.-%, olive oil in the range of 10 to 15 wt.-%, shea butter in the range of 10 to 25 wt.-%, bees wax in the range of 10 to 25 wt.-%, tea tree oil of 0.02 to 2 wt.-% and sunflower oil in the range of 10 to 15 wt.-%, each based on the total weight of the composition.

In a preferred embodiment of the present invention, the cream composition of the present invention comprises centella extract in the range of 0.1 to 0.5 wt.-%, borax in the range of 2 to 8 wt.-%, olive oil in the range of 10 to 15 wt.-%, shea butter in the range of 10 to 25 wt.-%, bees wax in the range of 10 to 25 wt.-%, tea tree oil of 0.02 to 2 wt.-% and sunflower oil in the range of 10 to 15 wt.-% and cromoglycate sodium in the range of 1 to 25 wt.-%, each based on the total weight of the composition.

In a preferred embodiment of the present invention, the cream composition comprises 1 to 12 wt.-% of water, preferably 5 to 12 wt.-%, preferably 5 to 20 wt.-%, preferably 10 to 20 wt.-%, preferably 10 to 30 wt.-%, preferably 20 to 30 wt.-%, preferably 20 to 40 wt.-%, based on the total weight of the composition.

In a preferred embodiment of the present invention, cromoglycate or a salt thereof is co-formulated or co-administered with a second active ingredient in the cream compositions of the present invention, preferably antihistamines, anti-inflammatory agents, or antimicrobial agents, in particular antibiotics, antivirals or antifungals, and combinations thereof.

Compositions:

In a preferred embodiment of the present invention, a bactericide is present in the cromoglycate-containing or cream compositions of the present invention.

In a preferred embodiment of the present invention, a fungicide is present in the cromoglycate-containing or cream compositions of the present invention.

In a preferred embodiment of the present invention, the cromoglycate-containing or cream compositions of the present invention comprise at least one carrier or excipient for delivery to ungulates. In a preferred embodiment, the composition comprises at least one additional agent selected from the group consisting of anti-oxidants, corrosion inhibitors, buffering agents, thickening agents, fragrances, coloring agents, stabilizing agents, UV stabilizers and anti-freeze agents.

In a preferred embodiment of the present invention, the cromoglycate-containing or cream compositions of the present invention have a pH-value of 4.5 to 9.5, preferably 4 to 9, preferably 5 to 9, preferably 5 to 9.5, preferably 6 to 9, preferably 4 to 8, preferably 5 to 8, preferably 6 to 8, or preferably 5 to 7.

In a preferred embodiment of the present invention, the compositions of the present invention, namely the cromoglycate-containing composition and/or the cream composition of the present invention, comprise cromoglycate or a salt thereof, in particular as an active ingredient, preferably as prophylactic and/or therapeutic agent. In a preferred embodiment of the present invention, cromoglycate or a salt thereof is the only active ingredient, in particular prophylactic and/or therapeutic active agent, in the compositions of the present invention, namely the cromoglycate containing composition and/or the cream composition of the present invention, for use in treatment of a dry hoof condition and/or for use in increasing hoof growth in ungulates.

In a preferred embodiment of the present invention, the compositions of the present invention, namely the cromoglycate-containing composition and/or the cream composition of the present invention, comprise cromoglycate or a salt thereof as the only active ingredient, in particular the only prophylactic and/or therapeutic agent.

In a preferred embodiment of the present invention, the compositions of the present invention, namely the cromoglycate-containing composition and/or the cream composition of the present invention, comprise cromoglycate or a salt thereof co-formulated or co-administered with a second active ingredient or several active ingredients. The second active ingredient is preferably an antihistamine, anti-inflammatory agent, or antimicrobial agent, in particular antibiotics, antivirals or antifungals, and combinations thereof.

In a further aspect, the present invention provides a method for increasing hoof growth in ungulates, wherein cromoglycate or a salt thereof or compositions of the present invention, namely the cromoglycate-containing composition and/or the cream composition of the present invention, is administered. In a preferred embodiment of the present invention, the method for increasing hoof growth in ungulates is a therapeutic or non-therapeutic method. In a preferred embodiment of the present invention, the method for increasing hoof growth in ungulates is a prophylactic method.

In a further aspect, the present invention provides a method for the treatment of a dry hoof condition, wherein cromoglycate or a salt thereof or compositions of the present invention, namely the cromoglycate-containing composition and/or the cream composition of the present invention, is administered. In a preferred embodiment of the present invention, the method for the treatment of a dry hoof condition is a therapeutic or non-therapeutic method. In a preferred embodiment of the present invention, the method for the treatment of a dry hoof condition is a prophylactic method.

In a preferred embodiment of the present invention, the hoof can be treated by using cromoglycate or a salt thereof or compositions of the present invention, namely the cromoglycate-containing composition and/or the cream composition of the present invention, at least one time, preferably the hoof can be treated over a period of several days, preferably over a period of several weeks, preferably 4 weeks, preferably 8 weeks, preferably 12 weeks, preferably 16 weeks, preferably 20 weeks, preferably 30 weeks, or preferably 40 weeks. In a preferred embodiment, the hoof can be treated by using cromoglycate or a salt thereof or compositions of the present invention over the lifetime of the ungulate.

In a preferred embodiment, cromoglycate or a salt thereof or compositions of the present invention, namely the cromoglycate-containing composition and/or the cream composition of the present invention, is applied to ungulates at least one-time a day, preferably at least two-times a day, preferably at least three-times a day.

In the context of the present invention, ungulates are any members of diverse clade of primarily large mammals that includes odd-toed ungulates such as donkey and horses and even-toed ungulates such as buffalos, camels, deer, elephants, giraffes, goats, hippopotami, kettle, pigs and sheep. Preferably, the ungulates of the present invention are horses.

The hoof plays a key role in performance, through the effect on confirmation, on sensing, which is the moment of touching the ground determine gait, and on circulation, wherein a poor hoof quality will lead to lameness through poor blood supply to the bone. Maintenance of hooves in good quality will improve performance.

Typically, a hoof that appears dry does not have a good hoof wall composition and is of low hoof quality. The dry appearance is caused by oil fat and oil levels. Moisture is not measured on the hoof wall, which gives the appearance, but in the soul and coronary band. The composition, structure and circulation level of the hoof, in particular the inner hoof structure, determines the moisture content. A low moisture content indicates that the (inner) hoof structure is not well developed, and indicates that the hoof quality is not good and, hints, the hoof as a hole can not function well, leading to lower performance, in particular raising performance.

In the context of the present invention, a good hoof quality is characterized by a smooth, shiny hoof wall having prominent and even growth rings, the tubules of the wall can be seen as parallel lines that run from coronary band to the base. The hoof wall should be free from flares, cracks, ripples, grooves and bulges. Further, a good hoof quality is characterized by a healthy, normal moisture content. Hoof growth is an indicator of hoof quality. In the context of the present invention, the hoof growth and moisture content are both indicators for hoof quality. In particular, a good hoof quality is indicated by the specifications as set forth in Table 3.

In the context of the present invention, the term 'hoof growth' refers to the growth of the hoof in length. In particular, the hoof growth is measured by taking pictures in regular intervals. For each picture a reference sticker of defined and known size is put on the hoof and is used as reference for the measurements on the picture. With a sharp metal object a groove ("scratch") is made in the hoof. Preferably, to determine hoof growth the length distance between the coronary band of the hoof and the groove is measured, preferably in regular intervals, preferably on the outer surface of the hoof wall. Other typical individual texture markers can be used as well as reference, i.e. measure the distance between marker and the coronary band.

In the context of the present invention, preferably the term hoof growth in particular refers to the growth of the hoof wall, preferably measured on the outer surface of the hoof wall, in particular refers to the growth of the hoof wall, preferably measured on the outer surface of the hoof wall, and other structures. The hoof growth may also be determined on the surface of the hoof sole, in particular measuring the frog length. In particular, the term refers to the growth of the hoof wall and the frog, in particular, refers to the growth of the frog, preferably in length.

In the context of the present invention, the term "increasing hoof growth" in particular means that the hoof growth rate is increased or the speed of growth of the hoof is increased, in particular in comparison to an untreated hoof, preferably in comparison to an untreated hoof of good quality. Since the growth of a hoof of poor quality is regularly slower than the growth of a hoof of good quality, the present invention therefore also provides an increased hoof growth in comparison to untreated hooves of poor quality. Thus, the present invention in particular refers to increasing the hoof growth thereby improving the hoof quality in comparison to the hoof quality of untreated hooves, in particular untreated hooves of a good quality.

The present invention provides an increased hoof growth in ungulates. In case the hoof growth of the ungulate to be treated is poor the present invention therefor preferably provides a therapeutic treatment of a poor hoof growth. In case the hoof growth of the ungulate to be treated is regular, i.e. normal or healthy, the present invention preferably provides an increased hoof growth, preferably greater than in hooves of good quality of untreated hooves. Furthermore, the present invention provides for a good hoof quality, in particular provides a good hoof quality by increasing hoof growth.

Preferably, the increased hoof growth is increased in comparison to untreated healthy hooves.

In a furthermore preferred embodiment, the increased hoof growth is increased in comparison to untreated unhealthy hooves.

In a preferred embodiment, the present invention relates to the increase in hoof growth in ungulates, wherein the hoof growth in the ungulate to be treated is a poor hoof growth, which poor hoof growth is, in a preferred embodiment be characterized by a growth rate of less than 6 mm/30 days, preferably less than 5, 4, 3, 2 or 1 mm/30 days.

In a preferred embodiment of the present invention, a regular that means healthy or normal hoof growth, is characterized by a hoof growth of at least 6 mm/30 days, preferably 6 mm/30 days to 7 mm/30 days.

In a furthermore preferred embodiment, the increase in hoof growth in ungulates is an increase in hoof growth, wherein the hoof growth in the ungulates to be treated is normal that means healthy, most preferably is equal to or greater than 6 mm/30 day, preferably up to 7 mm/30 days.

The present invention provides in comparison to an untreated healthy hoof an improved hoof quality as among others indicated by an increased hoof growth. In comparison to an untreated unhealthy hoof also an increased hoof growth is observed as part of an increased overall hoof quality.

In a preferred embodiment of the present invention, the term "increasing hoof growth" means "increasing hoof growth speed", preferably "increasing hoof growth rate".

In the context of the present invention, the term 'increasing hoof growth' preferably also means an accelerated hoof growth, preferably a stimulated hoof growth, or preferably an initiated hoof growth.

In a preferred embodiment of the present invention, an increased hoof growth is a growth characterized by a hoof growth of at least 7.5 mm/30 days, preferably at least 8 mm/30 days, preferably at least 9 mm/30 days, preferably at least 10 mm/30 days or at least 11 mm/30 days.

In the context of the present invention the term 'treatment' means a therapeutic and/or prophylactic treatment so as to increase hoof growth in hooves in which the hoof growth is poor or to provide a desired hoof growth in adverse conditions.

In the context of the present invention, a prophylactic treatment, which is a prophylaxis or prevention, is a treatment to provide good hoof quality, in particular hoof growth, in a desired condition, e.g. in a normal, i.e. healthy growth, preferably even under adverse conditions.

In a preferred embodiment of the present invention, the hoof to be treated, preferably to be treated prophylactically and/or therapeutically, is preferably a non-inflammated hoof, preferably a hoof without laminitis.

In the context of the present invention, the term 'dry hoof condition' refers to a condition of a unbalanced water content in the hoof, decreased water content in the hooves, dried-out brittle hooves or hooves that show a tendency to spilt and fracture.

In the context or the present invention, unbalanced moisture content refers to a condition indicating a low water content in the hooves or a high water content in the hooves.

Preferred embodiments of the present invention are subject matter of dependent claims.

In the following, the present invention is described in more detail by way of the non-limiting examples and the accompanying FIGS. 1 to 6.

EXAMPLES

Example 1: Treatment of Healthy Horses with Cream Formulation With and Without Sodium Cromoglycate 1.1 Cream Formulations and Treatment Schedule Two cream formulations were prepared (cream 001 and cream 002). Cream 001 is an essential cream. Cream 002 is an essential cream to which sodium cromoglycate has been added (see Table 1). Three comparable groups of four horses each were formed. One group was treated with cream 001, one with cream 002 and one group was kept untreated to serve as a control group. All horses in good condition were kept untreated for two months to assure there would be no interference of any previous treatment ('reset period'). For the treatment over a period of two months, once a day cream was applied on the coronary band of each front-leg, 5 ml per foot ('treatment period'). During the reset and treatment period, measurements were performed.

TABLE 1

| Ingredients | Cream 001 (%) | Cream 002 (%) |
|---|---|---|
| Centella Extract | 0.1 | 0.1 |
| Borax (250 mg/ml) | 6.4 | 6.4 |
| 5% Sodium Cromoglycate (71.4 g/l) | | 20 |
| Olive Oil | 12.9 | 12.9 |
| Shea Butter | 20 | 20 |
| Bees Wax | 20 | 20 |
| Sunflower Oil | 12 | 12 |
| Tea Tree Oil | 0.1 | 0.1 |
| Water | 28.5 | 8.5 |
| Total | 100 | 100 |

TABLE 2

| cream ingredient | composition | c number | lower range | upper range | actual | units |
|---|---|---|---|---|---|---|
| Beeswax | linear wax monoesters and hydroxymonesters | C24-C34 | 35 | 45 | | % |
| | complex wax esters | | 15 | 27 | | % |
| | straight chain hydrocarbons | C27-C33 | 12 | 16 | | % |
| | free fatty acids | C24-C32 | 12 | 15 | | % |
| | free fatty alcohols | C28-C35 | | 1 | | % |
| Shea butter | oleic acid | C18:1 | 41 | 45 | | % |
| | stearic acid | C18:0 | 40 | 42 | | % |
| | linoleic acid | C18:2 | 5.7 | 6.4 | | % |
| | palmitic acid | C16:0 | 3.3 | 5 | | % |
| | unsaponifiables | | 4 | 8 | | |
| | tocopherol | | 100 | 150 | | % |
| Sunflower oil | linoelic acid | C18:2 | | | 59 | % |
| | oleic acid | C18:1 | | | 30 | % |
| | stearic acid | C18:0 | | | 6 | % |
| | palmitic acid | C16:0 | | | 5 | % |
| Olive oil | oleic acid | C18:1 | 55 | 83 | | % |
| | palmitic acid | C16:0 | 7.5 | 20 | | % |
| | linoleic acid | C18:2 | 3.5 | 21 | | % |
| | stearic acid | C18:0 | 0.5 | 5 | | % |
| | alpha linoleic acid | | 0 | 1.5 | | % |
| Tea tree oil | terpin-4-ol | | 30 | 48 | | % |
| | gamma terpinene | | 10 | 28 | | % |
| | alpha terpinene | | 5 | 13 | | % |
| | 1,8 Cineole | | 0 | 15 | | % |
| | alpha terpinolene | | 1.5 | 5 | | % |
| | alpha terpineol | | 1.5 | 8 | | % |
| | alpha pinene | | 1 | 6 | | % |
| | p-cymene | | 0.5 | 8 | | % |
| Centella asiatica | propylene glycol | | 98.5 | 99.5 | | % |
| | centella asiatica | | 0.5 | 1.5 | | % |

1.2 Measurements

Moisture and hoof growth were measured every 10 days. Blood routine analysis was performed every alternate week.

Moisture content was determined using a standard moisture meter (MT-10 moisture meter from Amprobe). Five replicate readings were taken for the following nine sections in the right and left foot: dorsal coronary, dorsal middle, dorsal bottom, solar toe, solar white line, solar sole, solar frog tip, solar frog base and solar heel. The replicate values were analyzed using statistical software (R, https://cran.r-project.org) and averaged to give a single final value per foot for each section. Parameters for the measurement of hoof quality are summarized in Table 3.

Hoof quality and growth were determined using digital imaging. Of each hoof, multiple digital images were made and the following sections were measured: dorsal hoof wall angle, frog area, frog length, heel angle, heel toe angle, heel toe length, hoof area, hoof groove length, lateral hoof wall deviation and medial hoof wall deviation. The images were processed and analyzed using image analysis software (ImageJ, http://imagej.nih.gov/ij/) and statistical software (R, https://cran.r-project.org).

TABLE 3

| parameter | measurement | hoof quality and hoof growth specifications of a hoof of good quality |
|---|---|---|
| coronary band | palpation, images | thick and spongy, hair flat against the hoof capsule, width of growth rings below the coronary band should be equal from toe to heel, absence of scales below the coronary band |
| hoof wall appearance | image | smooth, shiny, even growth rings, parallel tubules running from coronet to base, no cracks, flares, ripples, grooves or bulges, moisture ~25%, |
| hoof groove length | image | growth 6 mm per 30 days |
| sole texture | palpation | firm, slightly concave, uniform texture, thicker in the toe and heel areas |
| sole thickness | X ray | 0.5 to 1 inch |
| heel to bulb distance | lateral image | lower heel bulb desirable |
| heel width | solar image | a narrow width indicates contacted heel (quantitative values NA) |
| hoof angle and heel angle difference | lateral image | <10° C. |
| support length (heel toe length) | solar image | |
| frog-appearance | palpation | should be tough and rubbery, width 60-70% of its leg, moisture 50% |
| frog length | solar image | should be 2/3 of the total length of the hoof |
| frog area | solar image | |
| distance from the fetlock | lateral image | distance is not exceedingly large |
| hoof pastern axis (HPA) | X ray | dorsal surface of the fetlock when viewed from side should be parallel to the dorsal surface of the hoof |
| palmar angle | X ray | 3-5 degree in front and slightly higher in front foot |

Table 3 indicates the parameters, the measurement methods and the specifications for hoof quality and hoof growth, which evidence a hoof quality and a hoof growth of a healthy hoof.

Figure 2:
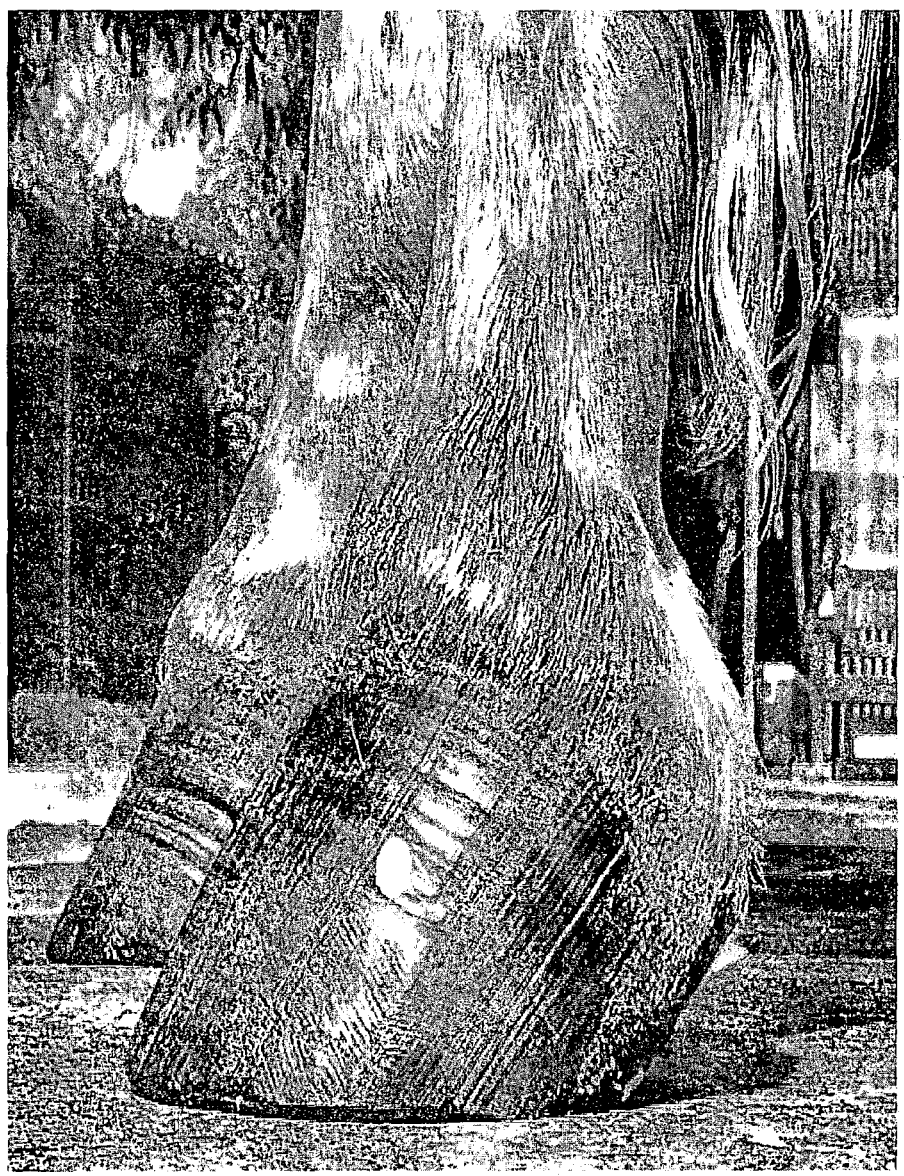
FIG. 2 is a picture of a hoof after treatment with cream with a marker on the hoof for measurement of hoof growth.
Figure 3:
FIG. 3 is a picture of a hoof before treatment showing a crack in the hoof.
Figure 4:
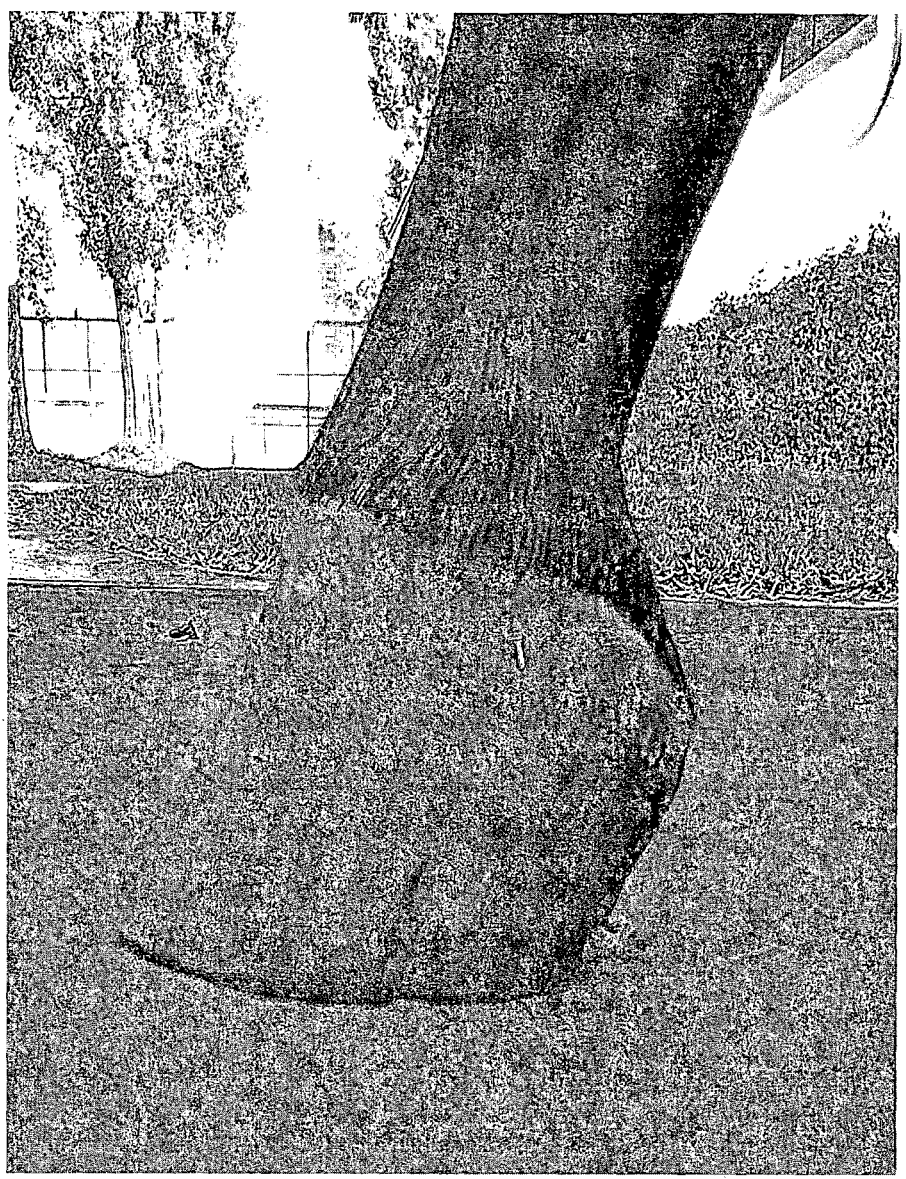
FIG. 4 is a picture of a hoof after 4 months of treatment.

The method for measuring the hoof growth is done as demonstrated in a photograph (see FIG. 2) and in schematic drawings (see FIGS. 5 and 6). Photograph of the hoof are taken in regular intervals. For each photograph a reference sticker of defined and known size is put on the hoof and is used as reference during the measurements on the photograph (FIGS. 2, 5, and 6). With a sharp metal object a groove ("scratch") is made in the hoof. The distance between the coronary band and the groove is measured in regular intervals. Other typical individual texture markers can be used as well as reference, i.e. measure the distance between the marker and the coronary band. The hooves are regularly trimmed, wherein the farrier cuts off the lower part of the hoof, like cutting a finger or toe nail for humans.

Figure 5A:
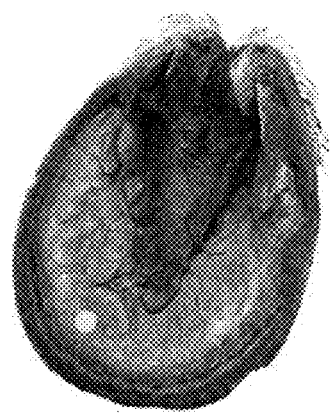
FIG. 5a is a picture of a bottom view of a hoof.
Figure 5B:
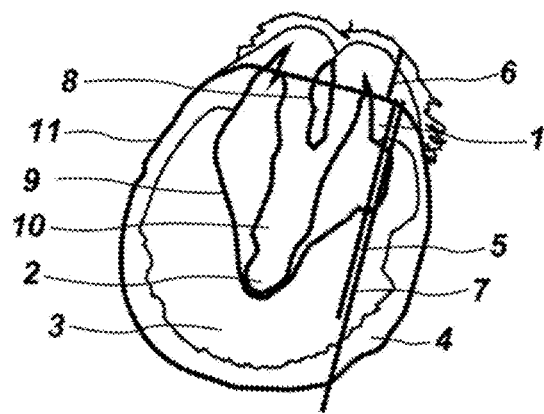
FIG. 5b is a schematic of a bottom view of a hoof.
Figure 6A:
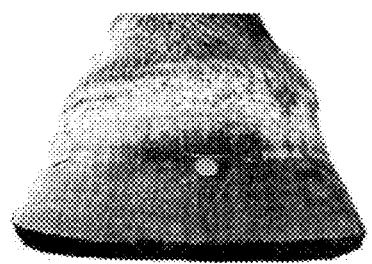
FIG. 6a is a picture of a front elevation view of a hoof.
Figure 6B:
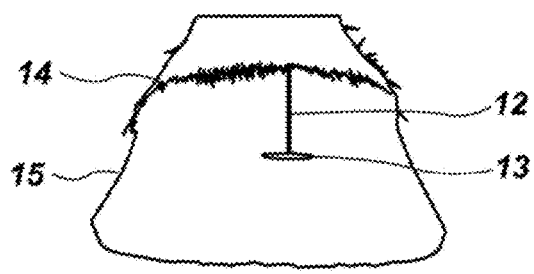
FIG. 6b is a schematic of a front elevation view of a hoof.

FIGS. 2, 5 and 6 show markers put on the hooves, allowing measurement of the hoof growth, in particular by measuring the groove length form the coronary band to the reference sticker in particular the reference sticker groove or texture marker. FIG. 6A indicates by way of a photograph and a schematic drawing (FIG. 6B) the preferred determination of measuring the hoof growth, in particular by measuring the distance between the coronary band and a set reference sticker on the outside of the hoof wall. FIG. 5A shows by way of a photograph and a schematic drawing (FIG. 5B) the frog length, which according to the present invention is also used to determine an increased growth of the hoof. Regarding FIG. 5B, 1 is the solar heel moisture, 2 is the solar frog tip moisture, 3 is the solar sole moisture, 4 is the solar white line moisture, 5 is the frog length, 6 is the heel bulb height, 7 is the heel toe length, 8 is the central sulci area, 9 is the lateral sulci area, 10 is the frog area, and 11 is the hoof area. Regarding FIG. 6B, 12 is the groove length, 13 is the groove, 14 is the coronary band, and 15 is the hoof wall.

1.3 Results

Out of the moisture measurements for nine sections of the hoof dorsal coronary, solar white line, solar sole, solar frog tip and solar frog base showed values that fall in the reliable region of the measurement device. An increase in moisture is observed within the dorsal coronary region (see Table 4). Hoof groove length increase was higher for cream 002 in comparison to cream 001 and control group (see Table 5).

TABLE 4

| Group | Treatment | Increase (%) |
|---|---|---|
| 1 | cream 001 | 6.49 |
| 2 | cream 002 | 15.64 |
| 3 | untreated horses | −1 |

TABLE 5

| Group | Description | Hoof Groove Length Increase (mm per 34 days) |
|---|---|---|
| 1 | cream 001 | 9.98 |
| 2 | cream 002 | 11.03 |
| 3 | untreated horses | 7.82 |

All hooves appear dry and scaly around the coronary band after the reset period (see FIG. 1). After treatment with cream 001 or cream 002 the hoof appeared hydrated and shiny and the coronary region had very few scales and dead tissue (see FIG. 2). The hoof of the untreated horses still appeared dry with scales around the coronary band.

The cream trial demonstrated that cream 001 and cream 002 applications on the coronary band result in a significant enhancement in moisture and hoof growth as compared to untreated horses. The moisture content of the untreated horses remained the same. Moisture increase in the coronary band was 6.4% for the base cream 001 and 15.6% for cream 002. The hoof growth was 7.8 mm for the untreated horses in 34 days, 9.9 mm with cream 001 and 11 mm with cream 002. The trial supports the benefits of cream application for hoof care. The treatment of hooves with hoof cream enhances hoof development and improves hoof quality.

Example 2: Treatment of a Quarter Crack Case with Hoof Cream

A severe quarter crack case was treated with cream 002 for 4 months. The cream application started after resecting the crack. Images were taken once in every month and the length of crack from the dorsal coronary band and resected area were measured using image analysis software (ImageJ, http://image.nih.gov/ij/).

Visible changes could be observed within a month. The crack started growing out with time as shown before the treatment (see FIG. 3) and after 4 months of treatment (see FIG. 4). The hoof grew faster and the crack healed faster than in previous cases.

The resected area of the hoof and width of resection also reduced with time (see Table 6).

TABLE 6

| | post treatment-1 month | post treatment-2 month | post treatment-3 month |
|---|---|---|---|
| lateral, mm | 15 | 21 | 28 |
| width of resection, | 24 | 16 | 11 |
| resected area, mm2 | 3911 | 3065 | 2512 |

This example demonstrates that not only the hoof wall grows that means increases in length but that specific parts of the hoof grow relatively more that means benefit more from the treatment, notably the frog leading to a better functioning of the hoof that means proprioception and support of circulation.

Example 3: Treatment of a Lame Horse with Hoof Cream

A 2 year old colt was diagnosed with lameness of 3 out of 5 (0 sound, 5 non weight-bearing lameness). The colt was treated with cream 002 on both front legs for 3 consecutive days. Upon lameness re-examination on day 4 the horse was found to be sound (0 out of 5). The analysis has shown that the treatment of the lameness was successful.

Example 4: Application of Cromoglycate Using Limb Perfusion

Method:

Healthy horses were treated by injecting 35 ml of 71 g/L sodium cromoglycate into each front limb using limb perfusion [12]. Standard blood analysis was carried out before and after treatment. The used devices are summarized in Table 7. Hoof quality and growth were determined over a period of time as described above.

TABLE 7

| device | manufacturer |
|---|---|
| thermal imager Ti25 | Fluke Corporation, Washington, |
| I-STAT | Abbott Diagnostics, Lake Forest, |
| Architect ci8200 | Abbott Diagnostics, Lake Forest, |
| Architect CD3700 | Abbott Diagnostics, Lake Forest, USA |

Results:

Example 4 demonstrates that sodium cromoglycate can be applied by limb perfusion. Limb perfusion with sodium cromoglycate was well tolerated by all horses. When pre and post treatment blood data were compared, a change in ionized calcium and a reduction in potassium were observed with not much effect on other blood parameters tested. Heart rate, temperature and gut sounds were normal at 24 h after injection.

The analysis has shown that the application of cromoglycate by limb perfusion increases hoof growth and improves hoof quality.

Example 5: Application of Cromoglycate Using Inhalation

Method:

Gas mix system and the Air-ONE nebuliser were prepared and operated as per manufacturer's instructions. For each treatment the nebuliser was loaded with 70 ml of 70 g/l sodium cromoglycate solution per horse. Treatment was continued until all 70 ml had been inhaled (between 20 to 30 minutes). Horses were treated at 2 day intervals for at least 1 and up to to 3 weeks. Standard blood analysis was carried out on Abbott i-STAT systems, Abbott Architect ci8200 and Architect Celldyn CD3700 before and after treatment. Micro-circulation was measured during inhalation using PeriFlux System 5000. The used devices are summarized in Table 8. Hoof quality and growth were determined as described above.

TABLE 8

| device | manufacturer |
| --- | --- |
| Air-ONE nebuliser incl. mask | Hippomed/Neu-Tec GmbH, Steinhagen, FRG |
| gas mix system | Dodhys Medical Ltd, Sharjah, UAE |
| gasses: N2, 02, C02 | AIRTEC Total Gas solutionsLLC, Dubai, UAE |
| I-STAT | Abbott Diagnostics, Lake Forest, USA |
| Architect ci8200 | Abbott Diagnostics, Lake Forest, USA |
| Architect CD3700 | Abbott Diagnostics, Lake Forest, USA |
| PeriFlux System 5000 | Perimed, Jafalla, Sweden |

Results:

Repeated inhalation with sodium cromoglycate was well tolerated by all horses. Calcium was effected upon treatment. The inhalation activates micro-circulation and improves digestion, coat and hoof quality.

The analysis has shown that the application of cromoglycate by inhalation increases hoof growth and improves hoof quality.

Example 6: Application of Cromoglycate Using Intravenous Fluid Therapy

Method:

70 ml of 70 g/l sodium cromoglycate was added to 1 liter of either NaCl or Hartmann's solution for the preparation of the intravenous fluid (see Table 10). Routine equine intravenous fluid therapy was carried out twice per week for 4 weeks. Standard blood analysis was carried out on Abbott i-STAT systems, Abbott Architect ci8200 and Architect Celldyn CD3700 before and after treatment. Micro-circulation was measured during treatment using PeriFlux System 5000. The used devices are summarized in Table 9. Hoof quality and growth were determined as described above.

TABLE 9

| device | manufacturer |
| --- | --- |
| I-STAT | Abbott Diagnostics, Lake Forest, USA |
| Architect ci8200 | Abbott Diagnostics, Lake Forest, USA |
| Architect CD3700 | Abbott Diagnostics, Lake Forest, USA |
| PeriFlux System | Perimed, Jafalla, Sweden |

TABLE 10

| ingredients | concentration (g/l) |
| --- | --- |
| sodium cromoglycate | 70 |
| sterile NaCl solution for injection | 9 |
| sterile Hartmann's solution for | 11.7 |

Results:

Repeated fluid therapy with sodium cromoglycate was well tolerated by all horses. Calcium was effected upon treatment. The fluid infusion improves digestion, coat and hoof quality.

The analysis has shown that the application of cromoglycate by an intravenous fluid increases hoof growth and improves hoof quality.

REFERENCES

[1] Cromolyn: Toxicology data network.

[2] E W Alton and A A Norris. Chloride transport and the actions of nedocromil sodium and cromolyn sodium in asthma. *J Allergy Clin Immunol,* 98(5 Pt 2):S102-5; discussion S105-6, November 1996.

[3] I L Bernstein. Cromolyn sodium. *Chest,* 87(1 Suppl): 68S-73S, January 1985.

[4] F. C Buonomo. Accelerating animal hoof growth with somatotropin. U.S. Pat. No. 5,962,416.

[5] S. Caddel and R. Stanback. The hoof and its relation to balance and soundness. *Equinews,* 2(1).

[6] Alan M Edwards. The discovery of cromolyn sodium and its effect on research and practice in allergy and immunology. *Journal of Allergy and Clinical Immunology,* 115(4):885-888, 2005.

[7] Alan M Edwards, Michael T Stevens, and Martin K Church. The effects of topical sodium cromoglycate on itch and flare in human skin induced by intradermal histamine: a randomised double-blind vehicle controlled intra-subject design trial. *BMC Res Notes,* 4:47, 2011.

[8] Hoof journal (http://horse-journal.com/content/content/16601/hoof-dressings_story.pdf). Hoof dressing: Shine is different from trying to restore hoof integrity.

[9] Yao-lin Liu, Fung-Rong Hu, I-Jong Wang, Wei-Li Chen, and Yu-Chih Hou. A double-masked study to compare the efficacy and safety of topical cromolyn for the treatment of allergic conjunctivitis. *J Formos Med Assoc,* 110(11): 690-4, November 2011.

[10] Tatsuya Oka, Janet Kalesnikoff, Philipp Starkl, Mindy Tsai, and Stephen J Galli. Evidence questioning cromolyn's effectiveness and selectivity as a 'mast cell stabilizer' in mice. *Lab Invest,* 92(10):1472-82, October 2012.

[11] C. F. Owen. Mast cell stabilizers to prevent or treat laminitis. WO 2010/126544 A1.

[12] S. E. Palmer and P. M. Hogan. How to perform regional limb perfusion in the standing horse. volume 45 of *AAEP Proceedings* 1999.

[13] M. J. Pautienis, R. Shakalis, and R. Tricca. The science behind modern hoof conditioners: How the hoof structure works.

[14] Paul H Ratner, Paul M Ehrlich, Stanley M Fineman, Eli O Meltzer, and David P Skoner. Use of intranasal cromolyn sodium for allergic rhinitis. *Mayo Clin Proc,* 77(4): 350-4, April 2002.

[15] J D Reilly, L Hopegood, L Gould, and L Devismes. Effect of a supplementary dietary evening primrose oil mixture on hoof growth, hoof growth rate and hoof lipid fractions in horses: a controlled and blinded trial. *Equine Vetl Suppl*, (26):58-65, September 1998.

[16] Sanofi-Aventis. Intal forte (5 mg cfc-free): Sodium cromoglycate for oral inhalation.

[17] Hye-Young Shin, Jung-Sook Kim, Nyeon-Hyoung An, Rae-Kil Park, and Hyung-Min Kim. Effect of disodium cromoglycate on mast cell-mediated immediate-type allergic reactions. *Life Sci*, 74(23):2877-87, April 2004.

[18] M T Stevens, A M Edwards, and J B L Howell. Sodium cromoglicate: an ineffective drug or meta-analysis misused? *Pharm Stat*, 6(2):123-37, 2007.

[19] R. W. L. Vroom. Composition for the treatment of hoof conditions in hoofed animals. Patent, EP1067835 A1, April 2001.

[20] E Wells and J Mann. Phosphorylation of a mast cell protein in response to treatment with anti-allergic compounds. implications for the mode of action of sodium cromoglycate. *Biochem Pharmacol*, 32(5):837 42, March 1983.

[21] Samia Yazid, Giovanna Leoni, Stephen J Getting, Dianne Cooper, Egle Solito, Mauro Perretti, and Roderick J Flower. Antiallergic cromones inhibit neutrophil recruitment onto vascular endothelium via annexin-al mobilization. *Arterioscler Thromb Vasc Biol*, 30(9):1718-24, September 2010.

[22] O Zegarra-Moran, S Lantero, O Sacco, G A Rossi, and L J Galietta. Insensitivity of volume-sensitive chloride currents to chromones in human airway epithelial cells. *Br J Pharmacol*, 125(6):1382-6, November 1998.

[23] Eyal Zur. Topical use of sodium cromoglicate (cromolyn sodium) to treat atopic dermatitis and other skin allergies. *Int J Pharm Compd*, 16(5):386-93, 2012.

The invention claimed is:

1. A method for increasing hoof growth in ungulates comprising: administering an effective amount of at least one of selected from the group of cromoglycate and a salt of cromoglycate to the ungulate wherein the ungulate has a dry hoof condition.

2. The method according to claim 1, wherein the hoof growth is increased by at least 5% in comparison to untreated hooves.

3. The method according to claim 1, wherein the increase of the hoof moisture content is higher than in untreated hooves.

4. The method according to claim 1, wherein the salt of cromolycate is sodium cromoglycate.

5. The method according to claim 1, wherein the ungulate is a horse.

6. The method according to claim 1, wherein the cromoglycate or a salt thereof is applied in the form of a solid or liquid cromoglycate-containing composition.

7. The method according to claim 6, wherein the cromoglycate-containing composition is a cream composition comprising centella extract, borax, olive oil, shea butter, bees wax and sunflower oil.

8. The method according to claim 6, wherein the cromoglycate-containing composition comprises 0.1 to 40% by weight of cromoglycate or a salt thereof.

9. The method according to claim 7, wherein the cromoglycate-containing composition comprises 0.1 to 40% by weight of cromoglycate or a salt thereof.

10. The method of claim 1, the method comprising: administering the effective amount of at least one of selected from the group of cromoglycate and a salt of cromoglycate to the ungulate, the ungulate not having laminitis.

11. The method according to claim 1, wherein the increase of the hoof moisture content is at least 10% higher than in an untreated hoof.

12. A method for increasing hoof growth in an ungulate comprising: applying an effective amount of a cromoglycate-containing composition to the ungulate; and wherein the cromoglycate-containing composition comprises at least one of cromoglycate and a salt thereof on a coronary band of a hoof of the ungulate.

13. The method according to claim 12, wherein applying the effective amount of the cromoglycate-containing composition increases a hoof moisture content to treat a dry hoof condition.

14. The method according to claim 12, wherein the cromoglycate-containing composition is applied in the form of a solid or liquid cromoglycate-containing composition.

15. The method according to claim 12, wherein the cromoglycate-containing composition is a cream composition comprising centella extract, borax, olive oil, shea butter, bees wax and sunflower oil.

16. The method according to claim 12, wherein the cromoglycate-containing composition comprises 0.1 to 40% by weight of cromoglycate or a salt thereof.

17. The method according to claim 12, wherein the cromoglycate-containing composition comprises 0.1 to 25% by weight of cromoglycate or a salt thereof.

* * * * *